(12) United States Patent
Bonde et al.

(10) Patent No.: US 8,340,785 B2
(45) Date of Patent: Dec. 25, 2012

(54) SELF EXPANDING ELECTRODE CUFF

(75) Inventors: Eric H. Bonde, Minnetonka, MN (US);
Roy L. Testerman, New Hope, MN (US); Timothy P. Herbert, Maple Grove, MN (US); Mark A. Christopherson, Shoreview, MN (US); Jesse D. Geroy, North Saint Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 847 days.

(21) Appl. No.: 12/114,352

(22) Filed: May 2, 2008

(65) Prior Publication Data

US 2009/0276024 A1    Nov. 5, 2009

(51) Int. Cl.
*A61N 1/05* (2006.01)

(52) U.S. Cl. ............. 607/118; 607/1; 607/2; 607/115; 607/116

(58) Field of Classification Search .................. None
See application file for complete search history.

(56) References Cited

U.S. PATENT DOCUMENTS

| | | |
|---|---|---|
| 3,654,933 A | 4/1972 | Hagfors |
| 3,774,618 A | 11/1973 | Avery |
| 4,374,527 A | 2/1983 | Iversen |
| 4,379,462 A | 4/1983 | Borkan et al. |
| 4,512,351 A | 4/1985 | Pohndorf |
| 4,573,481 A | 3/1986 | Bullara |
| 4,602,624 A | 7/1986 | Naples et al. |
| 4,628,614 A | 12/1986 | Thompson |
| 4,649,936 A | 3/1987 | Ungar et al. |
| 4,838,272 A | 6/1989 | Lieber |
| 4,940,065 A | 7/1990 | Tanagho et al. |
| 4,967,755 A | 11/1990 | Pohndorf |
| 5,038,781 A | 8/1991 | Lynch |
| 5,095,905 A | 3/1992 | Klepinski |

(Continued)

FOREIGN PATENT DOCUMENTS

EP    0865800    9/1998

(Continued)

OTHER PUBLICATIONS

A. Schwartz et al., "Therapeutic Electrical Stimulation of the Hypoglossal Nerve in Obstructive Sleep Apnea", Arch Otolaryngol Head Neck Surg., vol. 127, Oct. 2001, pp. 1216-1223.

(Continued)

*Primary Examiner* — Carl H Layno
*Assistant Examiner* — Deborah Malamud
(74) *Attorney, Agent, or Firm* — Dicke, Billig & Czaja PLLC

(57) ABSTRACT

An expandable electrode cuff of an implantable stimulation system that includes a base member, a first flange member extending from a proximal end along a first side wall of the base member to a first distal end, and a second flange member extending from a proximal end along a second side wall of the base member to a second distal end. The first flange member extends over both a top wall of the base member and the second flange member, and the second flange member extends over the top wall to form a lumen. The electrode cuff is capable of being advanced between a first position corresponding to both flange members extending over the top wall, a second position corresponding to the first flange member not extending over the top wall and the second flange member extending over the top wall, and a third position corresponding to both of the flange members not extending over the top wall.

10 Claims, 12 Drawing Sheets

U.S. PATENT DOCUMENTS

| | | | |
|---|---|---|---|
| 5,158,080 A | 10/1992 | Kallok | |
| 5,238,006 A | 8/1993 | Markowitz | |
| 5,265,624 A | 11/1993 | Bowman | |
| 5,282,468 A | 2/1994 | Klepinski | |
| 5,324,322 A | 6/1994 | Grill, Jr. et al. | |
| 5,344,438 A | 9/1994 | Testerman et al. | |
| 5,351,394 A | 10/1994 | Weinberg | |
| 5,398,596 A | 3/1995 | Fond | |
| 5,400,784 A | 3/1995 | Durand et al. | |
| 5,487,756 A | 1/1996 | Kallesoe et al. | |
| 5,505,201 A | 4/1996 | Grill, Jr. et al. | |
| 5,531,778 A | 7/1996 | Maschino | |
| 5,591,216 A | 1/1997 | Testerman et al. | |
| 5,634,462 A | 6/1997 | Tyler et al. | |
| 5,741,319 A | 4/1998 | Woloszko et al. | |
| 5,824,027 A | 10/1998 | Hoffer et al. | |
| 5,919,220 A | 7/1999 | Stieglitz et al. | |
| 5,938,596 A | 8/1999 | Woloszko et al. | |
| 6,066,165 A | 5/2000 | Racz | |
| 6,093,197 A | 7/2000 | Bakula et al. | |
| 6,366,815 B1 | 4/2002 | Haugland | |
| 6,456,866 B1 | 9/2002 | Tyler et al. | |
| 6,572,543 B1 | 6/2003 | Christopherson et al. | |
| 6,587,725 B1 | 7/2003 | Durand et al. | |
| 6,600,956 B2 * | 7/2003 | Maschino et al. | 607/118 |
| 6,907,293 B2 | 6/2005 | Grill | |
| 6,907,295 B2 | 6/2005 | Gross | |
| 7,054,692 B1 | 5/2006 | Whitehurst et al. | |
| 7,065,410 B2 | 6/2006 | Bardy | |
| 7,082,336 B2 | 7/2006 | Ransbury et al. | |
| 7,155,278 B2 | 12/2006 | King et al. | |
| 7,248,930 B1 | 7/2007 | Woloszko et al. | |
| 7,389,149 B2 | 6/2008 | Rossing et al. | |
| 7,463,934 B2 | 12/2008 | Tronnes et al. | |
| 7,630,771 B2 | 12/2009 | Cauller | |
| 7,634,315 B2 | 12/2009 | Cholette | |
| 7,644,714 B2 | 1/2010 | Atkinson et al. | |
| 7,680,538 B2 | 3/2010 | Durand et al. | |
| 7,725,195 B2 | 5/2010 | Lima et al. | |
| 7,787,959 B1 | 8/2010 | Morgan | |
| 7,809,442 B2 | 10/2010 | Bolea et al. | |
| 2004/0111139 A1 | 6/2004 | McCreery | |
| 2005/0010265 A1 | 1/2005 | Baru Fassio | |
| 2006/0030919 A1 | 2/2006 | Mrva et al. | |
| 2006/0103407 A1 | 5/2006 | Kakizawa et al. | |
| 2006/0195170 A1 | 8/2006 | Cohen | |
| 2006/0266369 A1 | 11/2006 | Atkinson et al. | |
| 2006/0271137 A1 | 11/2006 | Stanton-Hicks | |
| 2006/0282127 A1 | 12/2006 | Zealear | |
| 2007/0043411 A1 | 2/2007 | Foster | |
| 2007/0129780 A1 | 6/2007 | Whitehurst et al. | |
| 2007/0233204 A1 | 10/2007 | Lima et al. | |
| 2007/0239243 A1 | 10/2007 | Moffitt et al. | |
| 2007/0255379 A1 | 11/2007 | Williams et al. | |
| 2008/0046055 A1 | 2/2008 | Durand et al. | |
| 2008/0103545 A1 | 5/2008 | Bolea et al. | |
| 2008/0103570 A1 | 5/2008 | Gerber | |
| 2008/0132987 A1 | 6/2008 | Westlund et al. | |
| 2008/0172101 A1 | 7/2008 | Bolea et al. | |
| 2008/0172116 A1 | 7/2008 | Mrva et al. | |
| 2008/0177348 A1 | 7/2008 | Bolea et al. | |
| 2008/0319506 A1 | 12/2008 | Cauller | |
| 2009/0048580 A1 | 2/2009 | Gibson | |
| 2010/0047376 A1 | 2/2010 | Imbeau | |
| 2010/0094379 A1 | 4/2010 | Meadows et al. | |
| 2010/0174341 A1 | 7/2010 | Bolea et al. | |
| 2010/0198103 A1 | 8/2010 | Meadows et al. | |
| 2010/0241195 A1 | 9/2010 | Meadows et al. | |
| 2010/0241207 A1 | 9/2010 | Bluger | |

FOREIGN PATENT DOCUMENTS

| | | |
|---|---|---|
| WO | 2007140597 | 12/2007 |
| WO | 2008025155 | 3/2008 |
| WO | WO 2008/048471 | 4/2008 |
| WO | 2009048580 | 2/2009 |
| WO | 2009048581 | 4/2009 |
| WO | 2009135138 | 11/2009 |
| WO | 2009135140 | 11/2009 |
| WO | 2009140636 | 11/2009 |
| WO | 2010039853 | 4/2010 |
| WO | 2010059839 | 5/2010 |
| WO | 2010117810 | 10/2010 |

OTHER PUBLICATIONS

Eisele Article—David W. Eisele, MD et al., "Tongue neuromuscular and direct hypoglossal nerve stimulation for obstructive sleep apnea," Otolaryngologic Clinics of North America, Otolayngol Clin N Am 36 (2003) 501-510 (10 pages).

Goodall Article—Eleanor V. Goodhall et al., "Position-Selective Activation of Peripheral Nerve Fibers with a Cuff Electrode," IEEE Transaction on Biomedical Engineering, IEEE Service Center, Piscataway, NJ, US, vol. 43, No. 8, Aug. 1, 1996, pp. 851-856.

Naples Article—Gregory G. Naples et al., "A Spiral Nerve Cuff Electrode for Peripheral Nerve Stimulation," 8088 IEEE Transactions on Biomedical Engineering, 35. Nov. 1988, No. 11, New York, NY, pp. 905-915.

Oliven Article—Arie Oliven et al., "Upper airway response to electrical stimulation of the genioglossus in obstructive sleep apnea," Journal of Applied Physiology, vol. 95, pp. 2023-2029, Nov. 2003, www.jap.physiology.org on Sep. 18, 2006. (8 pages).

Schwartz Article—Alan R. Schwartz MD et al., Theraputic Electrical Stimulation of the Hypoglossal Nerve in Obstructive Sleep Apnea, Arch Otolaryngol Head And Neck Surg., vol. 127, Oct. 2001, pp. 1216-1223. Copyright 2001 American Medical Association. (8 pages.

Park Article—Jung I. Park MD, PhD, "Preoperative Percutaneous Cranial Nerve Mapping in Head and Neck Surgery", American Medical Association, 2003, (6 pages).

PCT, Notification of Transmittal of the International Search Report and the Written Opinion of the International Searching Authority, or the Declaration, Aug. 17, 2009, 21 pages.

Sahin et al., Chronic recordings of hypoglossal nerve activity in a dog model of upper airway obstruction, Journal of Applied Physiology, 1999, 11 pages.

* cited by examiner

SELF EXPANDING ELECTRODE CUFF

TECHNICAL FIELD

The invention relates generally to an implantable stimulation system for stimulating and monitoring soft tissue in a patient, and more particularly, the invention relates to an expandable electrode cuff for positioning an electrode of an implantable stimulation system about a nerve for stimulation and/or monitoring of nerve tissue.

BACKGROUND

Sleep apnea generally refers to the cessation of breathing during sleep. One type of sleep apnea, referred to as obstructive sleep apnea (OSA), is characterized by repetitive pauses in breathing during sleep due to the obstruction and/or collapse of the upper airway, and is usually accompanied by a reduction in blood oxygenation saturation.

One treatment for obstructive sleep apnea has included the delivery of electrical stimulation to the hypoglossal nerve, located in the neck region under the chin. Such stimulation therapy activates the upper airway muscles to maintain upper airway patency. In treatment of sleep apnea, increased respiratory effort resulting from the difficulty in breathing through an obstructed airway is avoided by synchronized stimulation of an upper airway muscle or muscle group that holds the airway open during the inspiratory phase of breathing. For example, the genioglossus muscle is stimulated during treatment of sleep apnea by a cuff electrode place around the hypoglossal nerve.

Because of the significant amount of movement in multiple directions that can take place under the chin, positioning an electrode to enable stimulation of the hypoglossal nerve becomes a significant challenge. On the one hand, placement of the electrode and lead in close proximity to the hypoglossal nerve can result in irritation to the nerve as a result of normal motion of the chin and neck, while on the other hand, without close adherence to the nerve, buildup of connective tissue between the nerve and the electrode and lead can occur, causing low thresholds, thereby reducing the effectiveness of the delivered stimulation by the device.

Another challenge in placing an electrode for nerve stimulation therapy relates to the tendency of the hypoglossal nerve to swell, which can result in the nerve being strangled by the electrode and lead. In addition, once the electrode cuff has initially been implanted, fibrosis tends to cause the location of the electrode cuff to become more fixed. Therefore, the first month post implant is critical to keep the electrode cuff properly positioned on the nerve, while at the same time it is important not to "suffocate" a swelling nerve. An additional challenge in placing the electrode for nerve stimulation results from the fact that stimulation currents need to be confined to the hypoglossal nerve in order to prevent other nearby nerves or muscles from being stimulated, which results in patient discomfort and loss of sleep. Therefore, what is needed is an improved electrode cuff that enables positioning of an electrode about a nerve.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DESCRIPTION OF EMBODIMENTS

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 1:
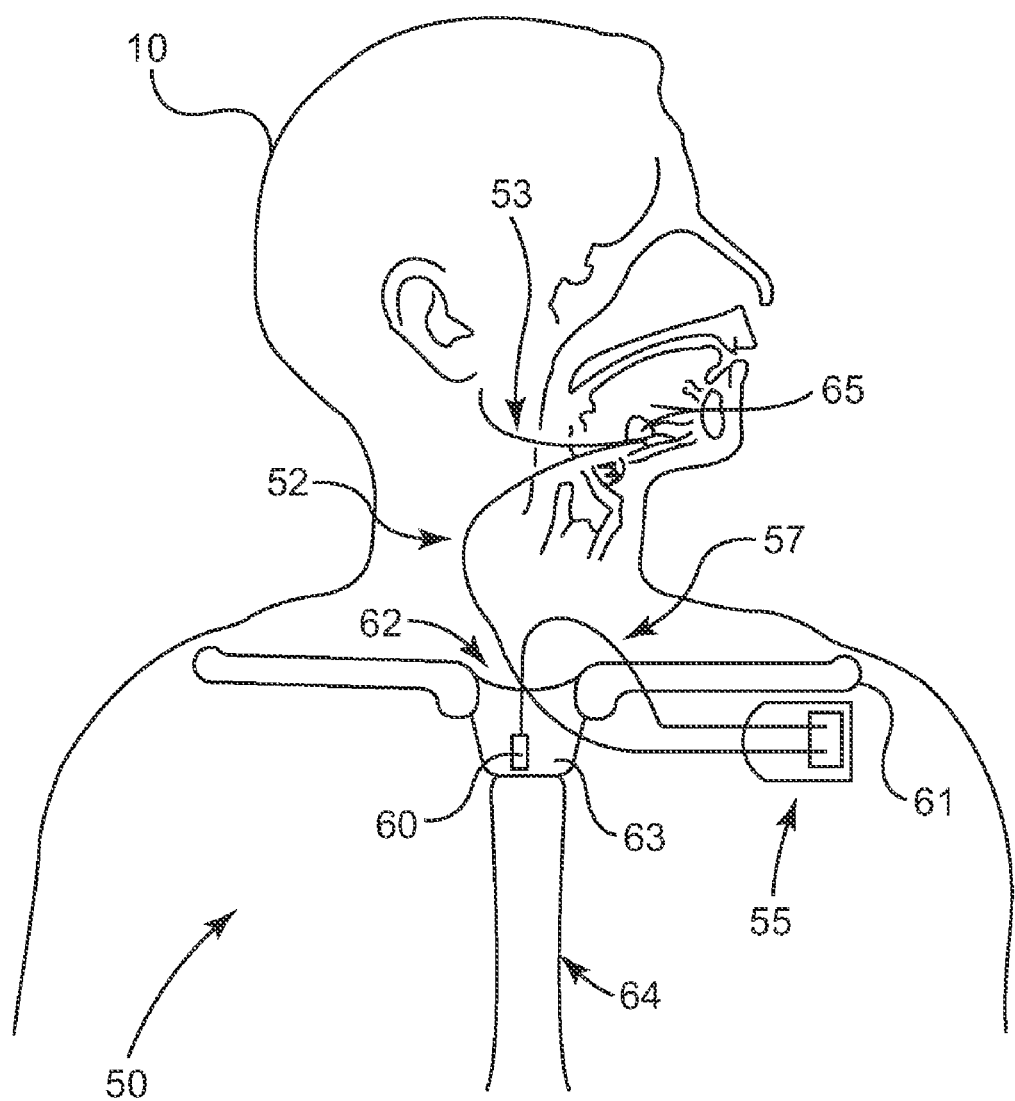
FIG. 1 is a schematic diagram of an implantable stimulation system that includes a self-expanding nerve cuff according to an embodiment of the invention.

FIG. 1 is a schematic diagram of an implantable stimulation system that includes a self-expanding nerve cuff according to an embodiment of the invention. As illustrated in FIG. 1, an example of an implantable stimulation system according to one embodiment of the invention includes an implantable pulse generator (IPG) 55, capable of being surgically positioned within a pectoral region of a patient 10, and a stimulation lead 52 electrically coupled with the IPG 55 via a connector (not shown) positioned within a connection port of the IPG 55. The lead 52 includes an electrode or electrode system 65 and extends from the IPG 55 so that the electrode system 65 is position around a desired nerve, such as the hypoglossal nerve 53 of the patient 10, to enable stimulation of the nerve 53, as described below in detail. An exemplary implantable stimulation system in which lead 52 may be utilized, for example, is described in U.S. Pat. No. 6,572,543 to Christopherson et al., incorporated herein by reference in its entirety, and further includes a sensor lead 57 electrically coupled to the IPG 55 and extending from the IPG 55 so that a sensor or transducer 60 can be positioned in the patient 10 for sensing of respiratory effort.

The sensor 60 may be a pressure sensor that is surgically implanted in a region that has pressure continuity with the intrapleural space, such as the suprasternal notch, the space between the trachea and esophagus, or by being attached to either of the trachea or esophagus. The sensor 60 may also be positioned intercostally, or secured in a position for sensing pressure at the posterior side of the manubrium. The suprasternal notch 62 and manubrium 63 of the sternum 64 are well known structures on the upper chest that are in anatomical continuity with the intrapleural space. It is also well known that changes in intrapleural pressure provide a characteristic respiratory effort waveform.

The location for placement of the sensor 60 is, at least in part, chosen as a function of a delay, i.e. the propagation time associated with a pressure waveform characteristic of respiratory effort propagating from the respiratory point of origin to the sensor position. The chosen location is also a function of the amount of filtering necessary to achieve a usable sensed signal at a particular location, i.e. the amount of filtering that is necessary to remove waveforms other than the waveform associated with the desired sensed characteristic, such as the filtering required to remove cardiac waveform activity, for example. The positioning of the sensor 60 enables the IPG 55 to receive respiratory effort waveform information utilized to determine increased respiratory effort, which is then used by the IPG 55 to control delivery of therapy in response to determined increases in respiratory effort.

Figure 2:
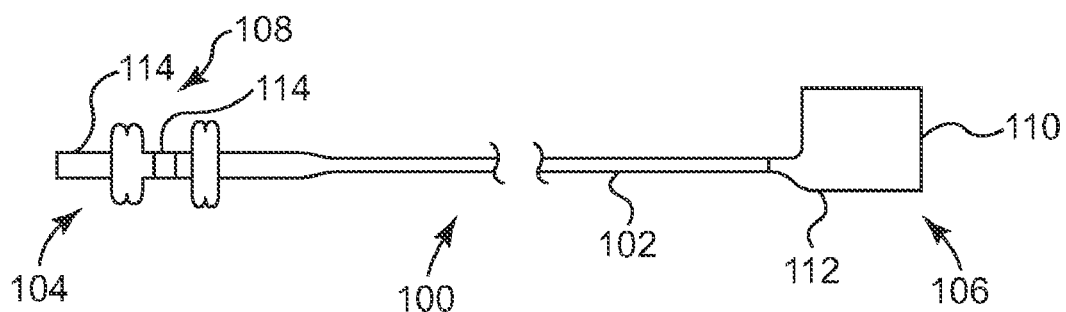
FIG. 2 is a side view of a lead utilized in an implantable stimulation system according to an embodiment of the invention.

FIG. 2 is a side view of a lead utilized in an implantable stimulation system according to an embodiment of the invention. As illustrated in FIG. 2, a lead 100 according to one embodiment includes a lead body 102 extending from a proximal end 104 to a distal end 106, with a connector 108 positioned at the proximal end 104 for electrically connecting the lead 100 to the IPG 55. An expandable electrode cuff 110, positioned at the distal end 106 of the lead body 102, is capable of being positioned around a nerve, such as a hypoglossal nerve for example, in order to strategically locate one or more electrodes 112 embedded within the electrode cuff 110 so as to be adjacent to the nerve when the electrode cuff 110 is positioned around the nerve. Conductors (not shown) are positioned within the lead body 102 to electrically connect the electrodes 112 and the connector 108 so that the electrodes 112 are electrically coupled to the IPG 55 via respective connector pins 114 of the connector 108, as is known in the art.

Figure 3:
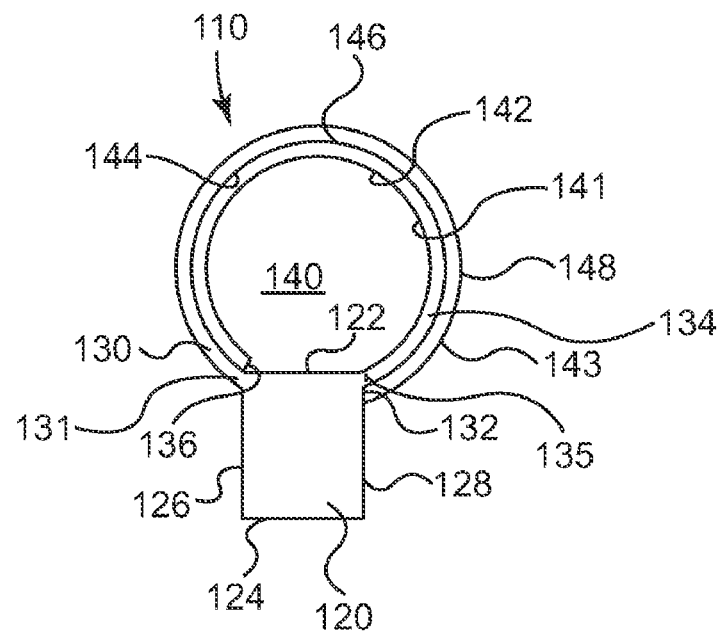
FIG. 3 is a front view of an expandable electrode cuff according to an embodiment of the invention.

FIG. 3 is a front view of an expandable electrode cuff according to an embodiment of the invention. As illustrated in FIG. 3, according to one embodiment, the expandable electrode cuff 110 is a single, unitary molded piece that includes a base portion 120 having a top wall 122 and a bottom wall 124 extending from a first side wall 126 to a second side wall 128. A first flange member 130 extends from a proximal end 131 to a distal end 312, and is located at the top wall 122 of the base portion 120 to extend from the first side wall 126 to the distal end 132. A second flange member 134 extends from a proximal end 135, and is located at the top wall 122 of the base portion 120 to extend from the second side wall 128 to the distal end 136. As will be described below, the electrode cuff 110 is expandable both during implantation of the lead 100 and electrode cuff 110, and after the electrode cuff 110 is positioned around a desired nerve for delivery of electrical stimulation therapy to the nerve.

During it's normal, unbiased state, prior to insertion around the nerve, the electrode cuff 110 is in a fully engaged position, shown in FIG. 3, in which the distal end 132 of the first flange member 130 is positioned adjacent to and may engage against the second side wall 128 at a location below the proximal end 135 of the second flange member 134 and below the top wall 122 of the base portion 120, and the distal end 136 of the second flange member 134 is positioned at a location above the proximal end 131 of the first flange member 130 and above the top wall 122 of the base portion 120 along the first side wall 126.

The first flange member 130 has a length greater than the second flange member 134 so that when the electrode cuff 110 is in the fully engaged position, the first flange member 130 and the second flange member 134 form a lumen 140 for receiving a nerve therein, with an inner side wall 141 of the second flange member 134 forming an inner wall 142 of the lumen 140 so as to position the electrodes 112 (shown in FIG. 2), which are embedded within the second flange member 134, adjacent to the nerve (not shown in FIG. 3).

In addition, when the electrode cuff 110 is in the fully engaged position, an inner side wall 144 of the first flange member 130 is positioned over and engages against an outer side wall 146 of the second flange member 134, and therefore an outer wall 148 of the first flange member 130 forms an outer wall 143 of the lumen 140. In this way, when the electrode cuff 110 is in the fully engaged position shown in FIG. 3, both the first flange member 130 and the second flange member 134 extend over the base portion 120, the first flange member 130 forms an outer portion of the electrode cuff 110, and the second flange member 134 forms an inner portion of the electrode cuff 110 for engaging the nerve. Depending on the size of the nerve, once positioned about a nerve, the electrode cuff 110 may be in either the fully engaged position of FIG. 3 or in a partially fully engaged position, wherein the distal end 132 of the first flange member 130 may be spaced from rather than engaged against the second side wall 128, and the distal end 136 of the second flange member 134 may be spaced from rather than aligned with the first side wall 126 at the top wall 122 of the base portion 120, as will be described below.

Figure 4:
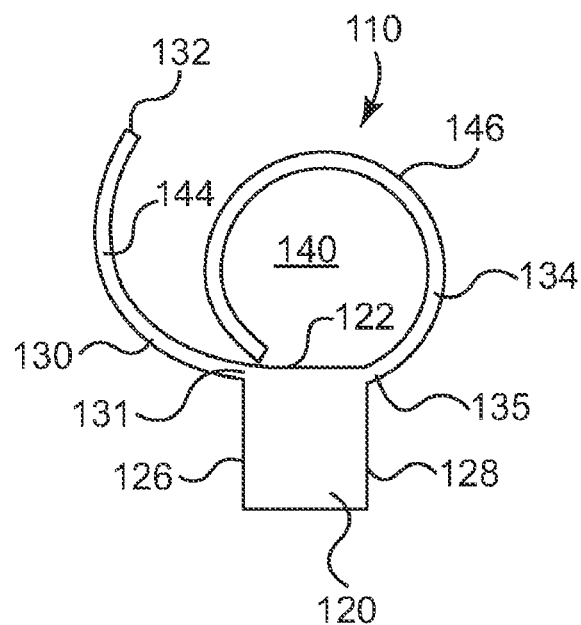
FIG. 4 is a front view of the expandable cuff of FIG. 3 in an intermediate open position according to an embodiment of the invention.

FIG. 4 is a front view of the expandable cuff of FIG. 3 in an intermediate open position according to an embodiment of the invention. As illustrated in FIG. 4, during positioning of the electrode cuff 110 over the desired nerve so that the nerve can be properly located within the lumen 140, the electrode cuff 110 is advanced from the fully engaged position shown in FIG. 3, to an intermediate position shown in FIG. 4, in which the distal end 132 of the first flange member 130 is advanced away from the second side wall 128, and the inner side wall 144 of the first flange member 130 is advanced away from the outer side wall 146 of the second flange member 134 so that the distal end 132 extends outward from and along the first side wall 126 of the base portion 120. As a result, when the electrode cuff 110 is in the intermediate open position, the first flange member 130 is not positioned so as to extend over the top wall 122 of the base portion 120, and the distal end 132 is no longer positioned below the top wall 122 of the base portion 120, while the second flange member 134 remains positioned to extend over the top wall 122 of the base portion 120 with the distal end 136 of the second flange member 134 positioned above the proximal end 131 of the first flange member 130. In addition, the inner side wall 144 of the first flange member 130 is no longer positioned over and adjacent to the outer side wall of 146 of the second flange member 134 when the cuff 110 is in the intermediate open position of FIG. 4.

Figure 5:
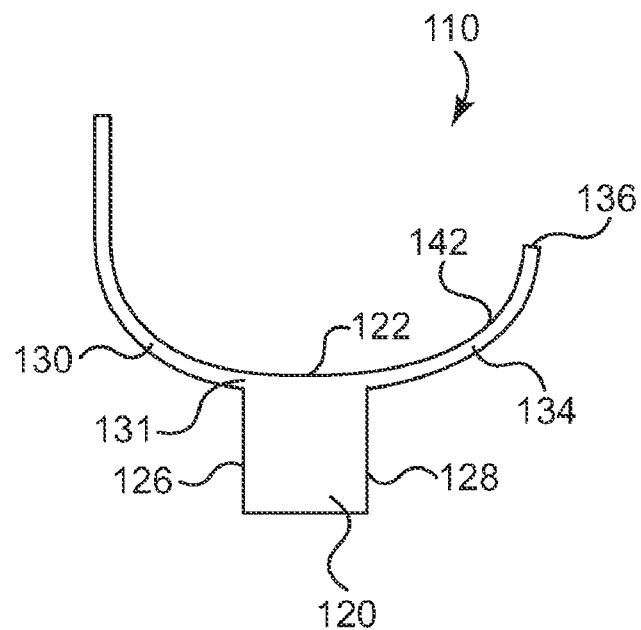
FIG. 5 is a front view of the expandable electrode cuff of FIG. 3 in a fully open position according to an embodiment of the invention.

FIG. 5 is a front view of the expandable electrode cuff of FIG. 3 in a fully open position according to an embodiment of the invention. As illustrated in FIG. 5, once the electrode cuff 110 is in the intermediate open position, the distal end 136 of the second flange member 134 is advanced away from the top wall 122 of the base portion 120 and the first side wall 126 so that rather than being positioned above the proximal end 131 of the first flange member 130, the distal end 136 of the second flange member 134 extends outward from the second side wall 128 so that the second flange member 134 does not extend over the second side wall 128 of the base portion 120, resulting in the inner wall 142 of the second flange member 134 no longer forming the lumen 140 when the cuff is in the fully open position of FIG. 5. As a result, when the electrode cuff 110 is in the fully open position, neither the first flange member 130 nor the second flange member 134 are positioned so as to extend over or near the top wall 122 of the base portion 120 of the electrode cuff 110, the inner side wall 144 of the first flange member 130 is no longer positioned over or near an outer side wall 146 of the second flange member 134, and the inner side wall 141 of the second flange member 134 no longer forms the inner wall 142 of the lumen 140. In this way, by enabling the electrode cuff 110 to be advanced between the fully engaged position, the intermediate open position, and the fully open position, the invention enables the cuff 110 to be more easily positioned over a nerve during implantation of the lead 100, as described below.

Figure 6:
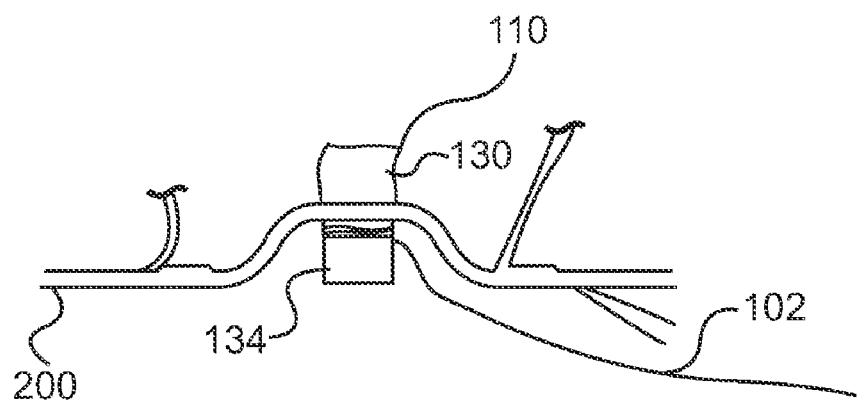
FIG. 6 is a schematic diagram illustrating positioning of an expandable electrode cuff over a desired nerve according to an embodiment of the invention.

FIG. 6 is a schematic diagram illustrating positioning of an expandable electrode cuff over a desired nerve according to an embodiment of the invention. As illustrated in FIG. 6, during the initial positioning of the lead and positioning of the electrode cuff 110 over a nerve, such as over a hypoglossal nerve 200, once the nerve 200 has been dissected out over a desired range, such as over 1-3 cm range, for example, the electrode cuff 110 is advanced from the normal, fully engaged position of FIG. 3 to the fully open position of FIG. 5 so that the inner flange 134 of the electrode cuff 110 is then inserted under the nerve 200 while in the fully open position, until the nerve 200 becomes positioned so as to be aligned with and against the top wall 122 of the base portion 120.

The inner flange member 134 is then released so that the inner flange member 134 becomes positioned around the nerve 200. According to one embodiment, prior to be advanced from the fully open position to the intermediate position, the base portion 120 of the electrode cuff 110 is positioned inward, towards the body of the patient. As a result, once positioned under the nerve 200, the electrode cuff 110 is advanced from the fully open position to the intermediate open position (FIG. 4) so that only the second flange member 134 is positioned over the top wall 122 of the base portion 120, enclosing the nerve 200. The outer flange member 130 is then released to be positioned around the nerve 200, resulting in the electrode cuff 110 being advanced from the intermediate open position to a final engaged positioned (see FIG. 7), with both the first flange member 130 and the second flange member 134 being positioned over the top wall 122 of the base portion 120, enclosing the nerve 200 within the lumen 140 formed by the flange members 130 and 134.

Figure 7:
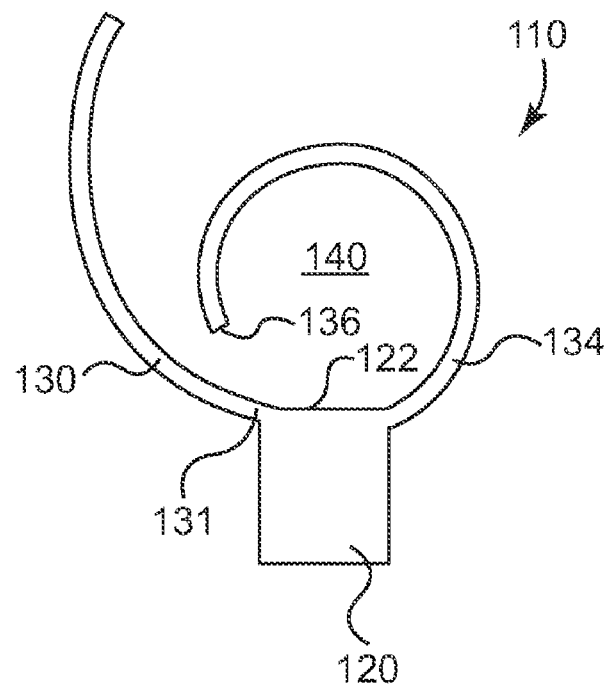
FIG. 7 is a front view of an expandable electrode cuff positioned about a nerve in an intermediate open position according to an embodiment.

FIG. 7 is a front view of an expandable electrode cuff positioned about a nerve in an intermediate open position according to an embodiment. As illustrated in FIG. 7, depending upon the circumference of the nerve 200, once the nerve 200 is positioned over the top wall 122 of the base portion 120 of the electrode cuff 110, and the inner flange member 134 is positioned about the nerve 200 during the advancement of the electrode cuff 110 from the fully open position of FIG. 5 to the intermediate open position of FIG. 7, the distal end 136 of the second flange member 134 may be positioned to be spaced further above the proximal end 131 of the first flange member 130 and further away from the first side wall 126 and the top wall 122 of the base portion 120 than when the electrode cuff 110 is in the intermediate open position of FIG. 4. As a result, the size of the lumen 140 can be increased relative to when the electrode cuff 110 is in the intermediate open position of FIG. 4 to accommodate the size of the nerve 200.

Figure 8:
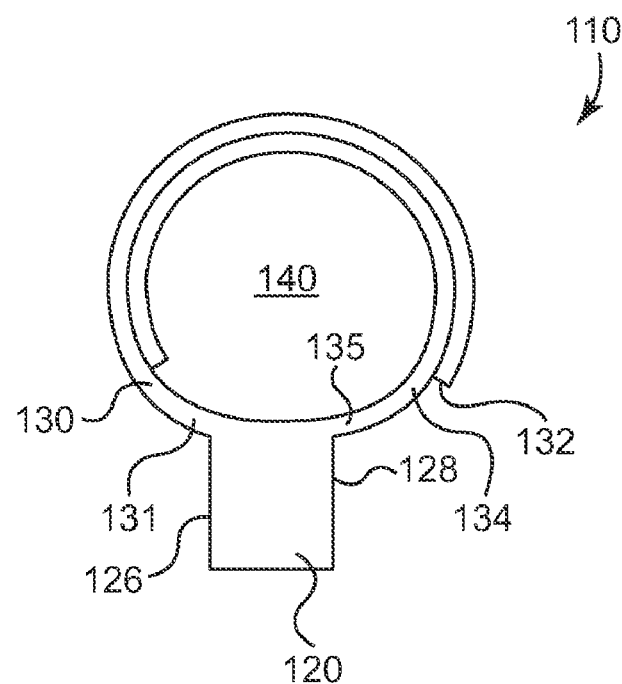
FIG. 8 is a front view of an expandable electrode cuff positioned about a nerve in a fully engaged position according to an embodiment.

FIG. 8 is a front view of an expandable electrode cuff positioned about a nerve in a fully engaged position according to an embodiment. Similarly, during the advancement of the electrode cuff from the intermediate open position of FIG. 7 to the fully engaged position during implant of the electrode cuff 110, the distal end 132 of the outer flange member 130 may be positioned to be spaced further away from the second side wall 128 of the base portion 120 than when the electrode cuff 110 is in the fully engaged position of FIG. 3, and to be above, rather than below the proximal end 135 of the second flange member 134 and the top wall 122 of the base portion 120, thereby increasing the size of the lumen 140 relative to when the electrode cuff 110 is in the fully engaged position of FIG. 3 prior to be implanted to accommodate the size of the nerve. Therefore, as illustrated in FIGS. 7 and 8, in order to accommodate the size of the nerve, the first and second flanges 130 and 134 can be advanced or expanded to increase the diameter of the lumen 140.

Figure 9:
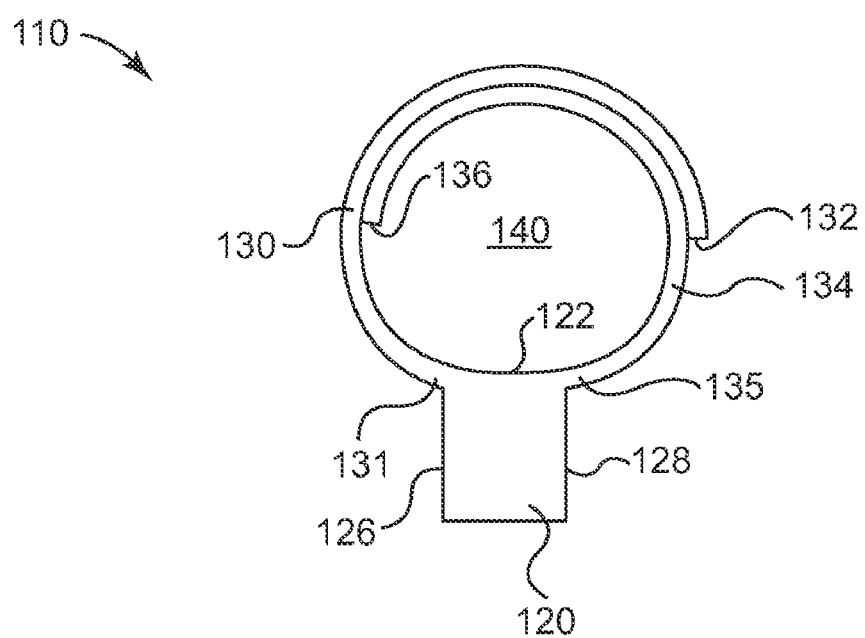
FIG. 9 is a front view of an expandable electrode cuff positioned around a nerve according to an embodiment of the invention.

FIG. 9 is a front view of an expandable electrode cuff positioned around a nerve according to an embodiment of the invention. If the small arteries that run along the side of the nerve are overly restricted by the electrode cuff 110, blood supply could be inhibited, causing temporary or permanent damage to the nerve. The inventors have found that approximately 25 mmHg is the approximate amount of pressure that may be applied to the nerve without restricting blood flow. As illustrated in FIG. 9, according to one embodiment, in order to address the effects of swelling of the hypoglossal nerve 200 that may sometimes occur, particularly after the initial trauma associated with implanting the electrode cuff 110, the first and second flange members 130 and 134 are expandable so that the circumference of the lumen 140 formed by the electrode cuff 110 is able to increase to accommodate increases in the diameter of the nerve 200 that occur subsequent to the initial positioning of the expandable electrode cuff 110 about the nerve 200. For example, during swelling of the nerve 200 subsequent to implant of the device 100, the first flange member 130 and the second flange member 134 expand so that the distal end 132 of the first flange member 130 becomes positioned to be spaced further away from the second side wall 128 of the base portion 120, and to be even further above, rather than below the proximal end 135 of the second flange member 134 and the top wall 122 of the base portion 120. At the same time, the distal end 136 of the second flange member 134 becomes positioned to be spaced further above the proximal end 131 of the first flange member 130 and further away from the first side wall 126 and the top wall 122 of the base portion 120, thereby further increasing the size of the lumen 140 to accommodate the swelling. As the swelling of the nerve 200 subsides, the first and second flange members 130 and 134 return towards the original fully engaged position about the nerve 200 that occurred at the time of implant.

Figure 10:
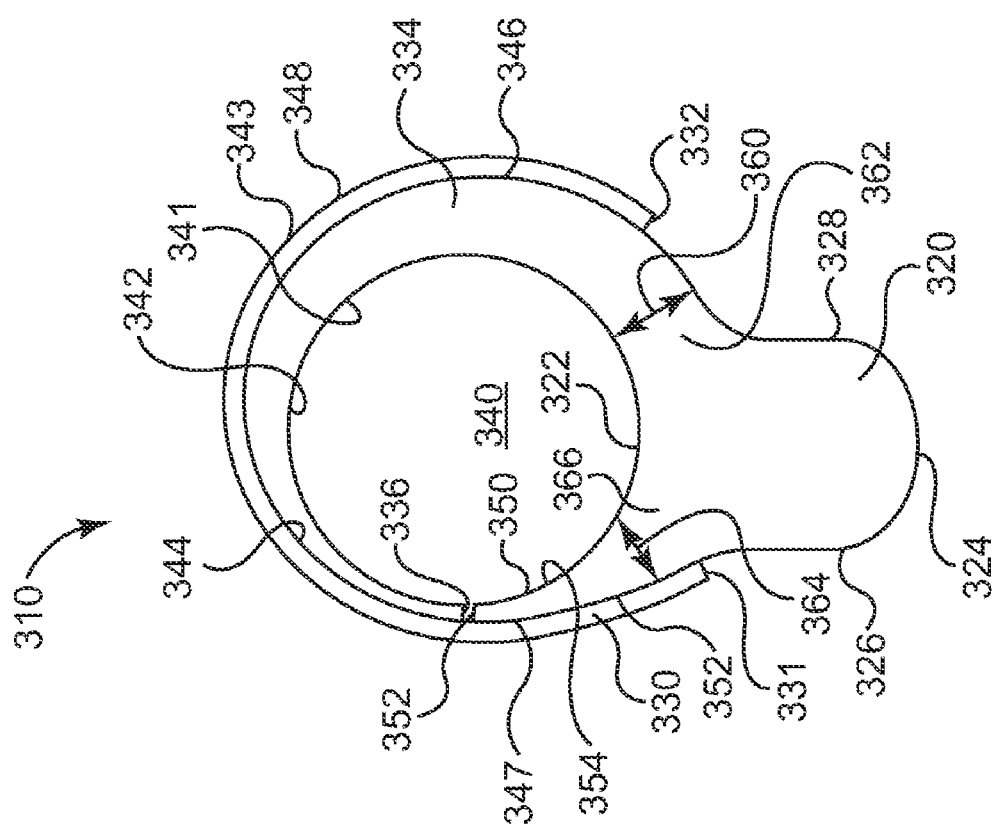
FIG. 10 is a front view of an expandable electrode cuff according to an embodiment of the invention.

FIG. 10 is a front view of an expandable electrode cuff according to an embodiment of the invention. As illustrated in FIG. 10, according to another embodiment, an expandable electrode cuff 310 includes a base portion 320 having a top wall 322 and a bottom wall 324 extending from a first side wall 326 to a second side wall 328, a first flange member 330, a second flange member 334, and a third flange member 350. The first flange member 330 is bonded at a proximal end 331 to the third flange member 350 along a portion of an outer wall 352 of the third flange member 350, and extends outward and over the top wall 322 of the base portion 320 from the first side wall 326 to a distal end 332. The second flange member 334 extends outward and over the top wall 322 of the base portion 320 from the second side wall 328 to a distal end 336. The third flange member 350 extends outward at the top wall 322 of the base portion 320 from the first side wall 326 to a distal end 352.

In the expandable electrode cuff 310 of the embodiment of FIG. 10, the base portion 320, second flange member 334 and the third flange member 350 are formed from a single, unitary molded piece, with the first flange member 330 bonded to the molded piece. As will be described below, the electrode cuff 310 is expandable both during implantation of the lead 100 and electrode cuff 310, and after the electrode cuff 310 is positioned around a desired nerve for delivery of electrical stimulation therapy to the nerve, similar to the electrode cuff 110 described above in the embodiment of FIGS. 3-5.

During it's normal, unbiased state, prior to insertion around the nerve, the electrode cuff 310 is in a fully engaged position, shown in FIG. 10, in which the first flange member 330 extends outward and over the top wall 322 of the base portion 320 from the first side wall 326 to the distal end 332, the second flange member 334 extends outward and over the top wall 322 of the base portion 320 from the second side wall 328 to the distal end 336, and third flange member 350 extends outward at the top wall 322 of the base portion 320 from the first side wall 326 to the distal end 352 so that the third flange member 350 does not extend over the top wall 332. In addition, while in the fully engaged position, the distal end 332 of the first flange member 330 is positioned adjacent to and engaged against an outer side wall 346 of the second flange member 334 and an outer side wall 347 of the third flange member 350, and the distal end 336 of the second flange member 334 is positioned adjacent to and may be engage against the distal end 352 of the third flange member 350 at a location along the first flange member 330.

The first flange member 330 has a length greater than the second flange member 334 so that when the electrode cuff 310 is in the fully engaged position, the first, second and third flange members 330, 334 and 350 form a lumen 340 for receiving a nerve therein, with an inner side wall 341 of the second flange member 134 and an inner side wall 354 of the third flange member 350 forming an inner wall 342 of the lumen 340 so as to position the electrodes 112 (shown in FIG. 2), which are embedded within the second flange member 334, adjacent to the nerve (not shown in FIG. 3). In addition, when the electrode cuff 310 is in the fully engaged position, an inner side wall 344 of the first flange member 330 is positioned over the outer side wall 346 of the second flange member 334 and the outer side wall 347 of the third flange member 350, and an outer wall 348 of the first flange member 330 forms an outer wall 343 of the lumen 340. In this way, when the electrode cuff 310 is in the fully engaged position shown in FIG. 10, both the first flange member 330 and the second flange member 334 extend over the base portion 320, the first flange member 330 forms an outer portion of the electrode cuff 310, and the second and third flange members 334 and 350 form an inner portion of the electrode cuff 310 for engaging the nerve. Depending on the size of the nerve, once positioned about the nerve, the electrode cuff 310 may be either in the fully engaged position of FIG. 10 or in a partially fully engaged position, wherein the distal end 332 of the first flange member 330 may be positioned along the outer side wall 346 of the second flange member 334 to be spaced further away from the second side wall 328 than shown in FIG. 10, and the distal end 336 of the second flange member 334 may be spaced further away from and not engaged against the distal end 352 of the third flange member 350, as will be described below.

Figure 11:
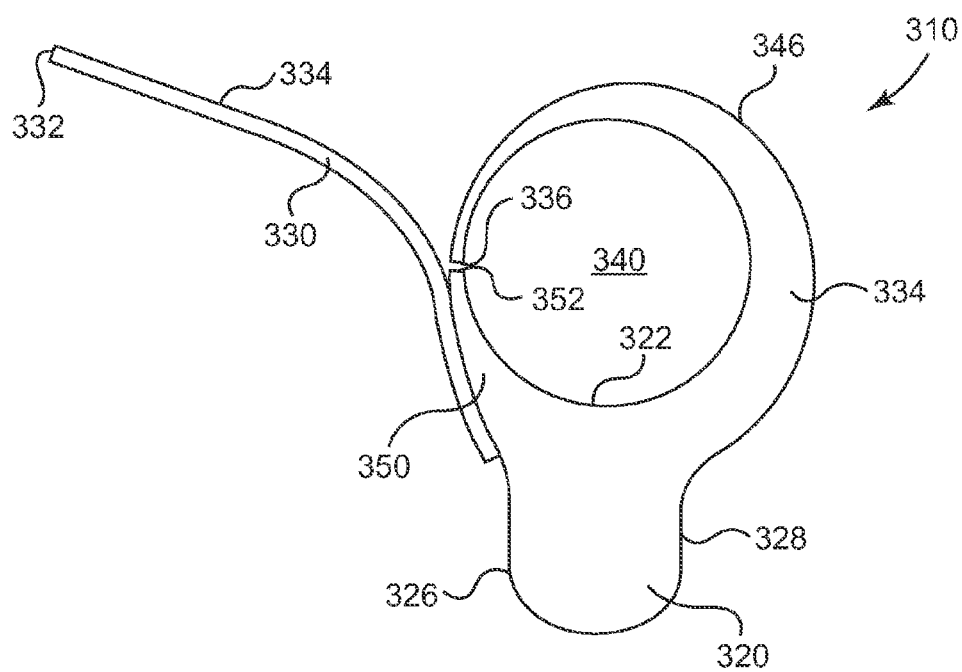
FIG. 11 is a front view of the expandable cuff of FIG. 10 in an intermediate open position according to an embodiment of the invention.

FIG. 11 is a front view of the expandable cuff of FIG. 10 in an intermediate open position according to an embodiment of the invention. As illustrated in FIG. 11, during positioning of the electrode cuff 310 over the desired nerve so that the nerve can be properly located within the lumen 340, the electrode cuff 310 is advanced from the fully engaged position shown in FIG. 10, to an intermediate position shown in FIG. 11 in which the distal end 332 of the first flange member 330 is advanced away from the second side wall 328, and the first flange member 330 is advanced away from the second flange member 334 so that the distal end 332 extends outward in an opposite direction from the first side wall 326 of the base portion 320. As a result, when the electrode cuff 310 is in the intermediate open position, the first flange member 330 is not positioned so as to extend over the top wall 322 of the base portion 320, while the second flange member 334 remains positioned to extend over the top wall 322 of the base portion 320, with the distal end 336 adjacent to the distal end 352 of the third flange member 350. In addition, the inner side wall 344 of the first flange member 330 is no longer positioned over and adjacent to the outer side wall 346 of the second flange member 334 when the cuff 310 is in the intermediate open position of FIG. 11.

Figure 12:
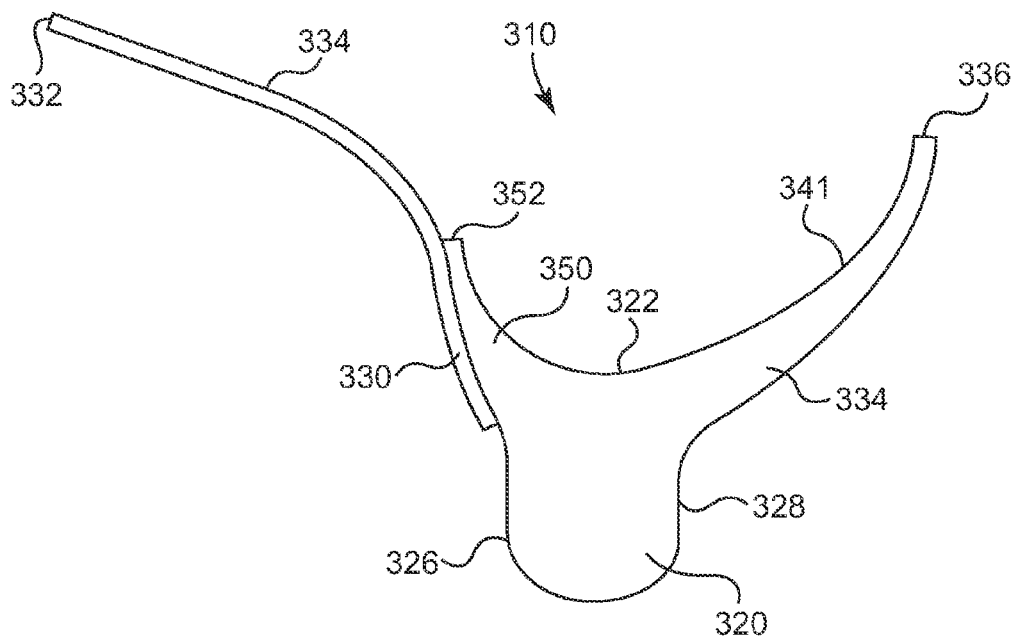
FIG. 12 is a front view of the expandable electrode cuff of FIG. 10 in a fully open position according to an embodiment of the invention.

FIG. 12 is a front view of the expandable electrode cuff of FIG. 10 in a fully open position according to an embodiment of the invention. As illustrated in FIG. 12, once the electrode cuff 310 is in the intermediate open position, the distal end 336 of the second flange member 334 is advanced away from the distal end 352 of the third flange member 350 and the second flange member 334 is advanced to no longer extend over the top wall 322 of the base portion 320 and the first side wall 326 so that the distal end 336 extends outward in the opposite direction from the second side wall 328, resulting in the inner wall 342 of the second flange member 334 no longer forming the lumen 340 when the electrode cuff 310 is in the fully open position of FIG. 12. As a result, when the electrode cuff 310 is in the fully open position, neither the first flange member 330 nor the second flange member 334 are positioned so as to extend over or near the top wall 322 of the base portion 320 of the electrode cuff 310, the inner side wall 344 of the first flange member 330 is no longer positioned over or near the outer side wall 346 of the second flange member 334, and the inner side wall 341 of the second flange member 334 no longer forms the inner wall 342 of the lumen 340.

In this way, by enabling the electrode cuff 310 to be advanced between the fully engaged position, the intermediate open position, and the fully open position, the electrode cuff 310 can be more easily positioned over a nerve during implantation of the lead 100, using the same method of implantation as described above in FIG. 6, for example. If desired, an adhesive material (not shown) could be added to the distal end 352 of the third flange member 350 in order to make a smoother transition at the distal end 352 and the inner wall 334 of the first flange member 330 during positioning of the electrode cuff 310 about the nerve.

As can be seen in FIGS. 10-12, the second flange member 334 according to one embodiment has a first thickness 360 along a proximal end 362 located at the top wall 322 of the base portion 120 along the second side wall 328, and a second thickness, less than the first thickness 360, at the distal end 336 of the second flange member 334, so that the second flange member 334 is tapered in thickness from the proximal end 362 to the distal end 336. Similarly, the third flange member 350 has a first thickness 364 along a proximal end 366 located at the top wall 322 of the base portion 320 along the first side wall 326, and a second thickness, less than the first thickness 364, at the distal end 352 of the third flange member 350, so that the third flange member 350 is tapered in thickness from the proximal end 366 to the distal end 352. While the inner flange member 334 of FIGS. 8-10 is shown to be tapered, it is understood that both the inner flange member 334 and the outer flange member 332 could be formed without being tapered. In addition, it is understood that the inner flange member 134 of FIGS. 3-5 may also be tapered as described in the embodiment of FIGS. 10-12.

The flange members described above may be formed from polyurethane, silicon or a blend of polyurethane and silicon. Furthermore, according to an embodiment, one of the flange members could be formed of polyurethane while the other is formed of silicon. If formed from silicone, then the durometer of the flange material range would be within a range of approximately 40 A-70 A. The thickness of the flange material could be from approximately 0.005 inches to 0.025 inches. Nominally, if the flange is formed of a polyurethane having a durometer of approximately 85 A, the flange would be 0.0075 inches thick. In the embodiment of FIGS. 10-12, the inner flange 334 is formed from molded polyurethane and the outer flange 330 is formed from a portion of a polyurethane tubing. In either embodiment, the polyurethane is formed to have a "memory" that enables the flange members to be biased towards the fully engaged positioned. The lumen 140, 340 may have an inner diameter between 0.050 and 0.400 inches, while according to an embodiment, the inner diameter is approximately 0.140 inches in the fully engaged position.

If the inner flange member 134, 334 is tapered, the respective proximal end 135 and 360 may have a thickness of approximately 0.025 to 0.030 inches, and the distal end 136, 336 may have a thickness of approximately 0.001 to 0.010 inches. This provides a strong mechanical connection to the sidewall and also provides the needed thickness to hold and strain relief the electrodes. According to one embodiment, the distal end 136, 336 has a thickness of 0.005 inches. Similarly, the distal end 352 of the third flange member 350 may have a thickness of approximately 0.001 to 0.010 inches, and according to an embodiment in which the distal end 336 of the second flange member 334, the distal end 352 of the third flange member would also have a thickness of approximately 0.005 inches.

Figure 13:
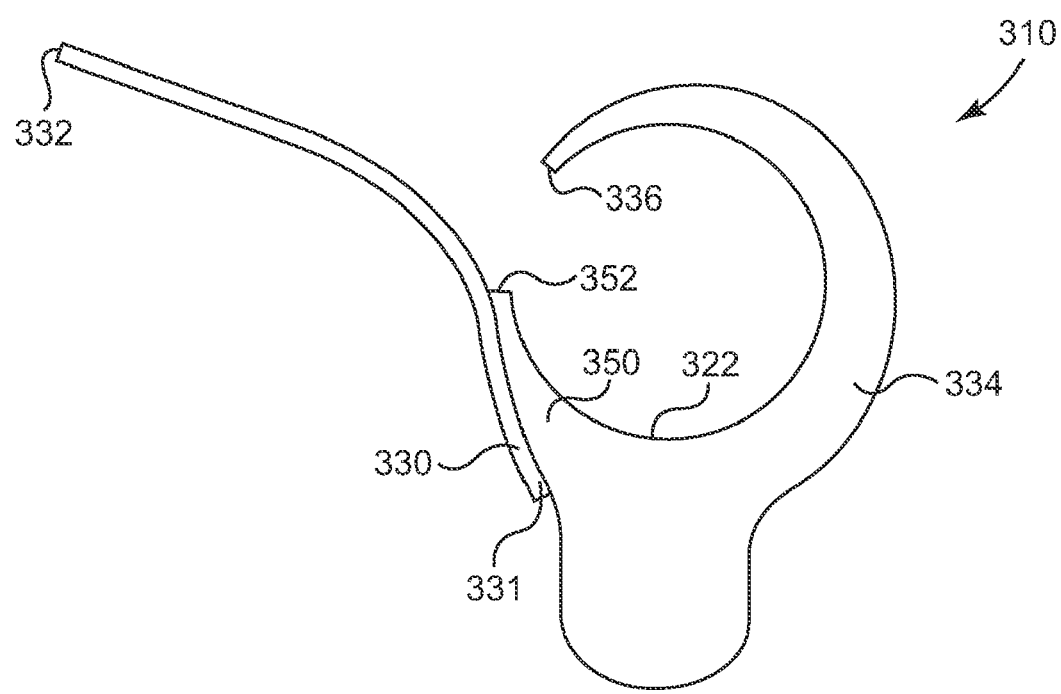
FIG. 13 is a front view of an expandable electrode cuff positioned about a nerve in an intermediate open position according to an embodiment.

FIG. 13 is a front view of an expandable electrode cuff positioned about a nerve in an intermediate open position according to an embodiment. As illustrated in FIG. 13, depending upon the circumference of the nerve 200, once the nerve 200 is positioned over the top wall 322 of the base portion 320 of the electrode cuff 310 and adjacent to the third flange member 350, and the second flange member 334 is positioned about the nerve 200 during the advancement of the electrode cuff 310 from the fully open position of FIG. 10 to the intermediate open position, the distal end 336 of the second flange member 334 may be positioned to be spaced further above the proximal end 331 of the first flange member 330 and the distal end 352 of the third flange member 350 than when the electrode cuff 310 is in the intermediate open position of FIG. 11. As a result, the size of the lumen 340 can be increased relative to when the electrode cuff 310 is in the intermediate open position of FIG. 11 to accommodate the size of the nerve 200 during positioning of the electrode cuff 310.

Figure 14:
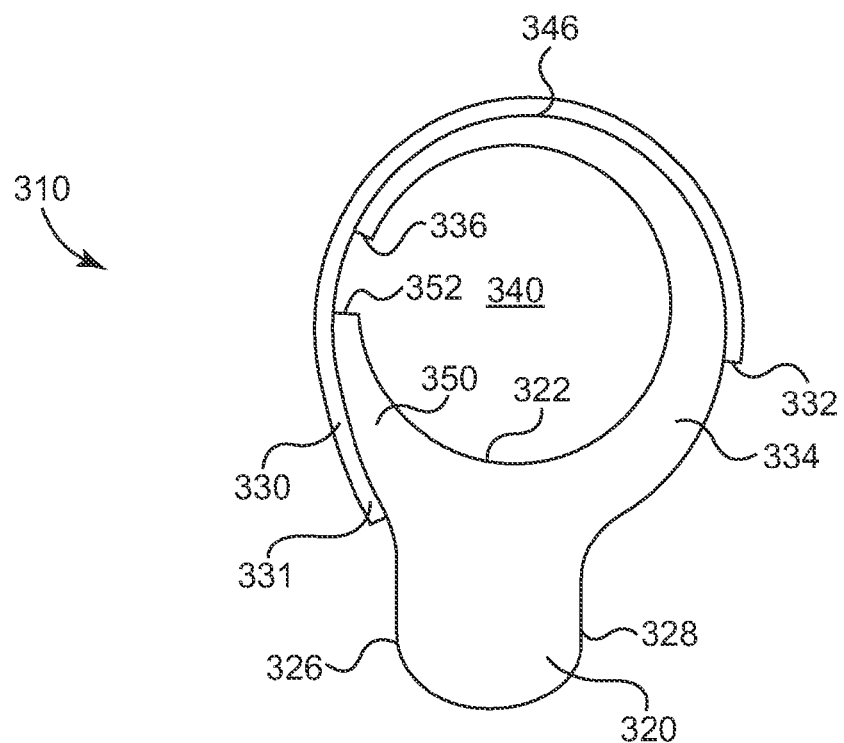
FIG. 14 is a front view of an expandable electrode cuff positioned about a nerve in a fully engaged position according to an embodiment.

FIG. 14 is a front view of an expandable electrode cuff positioned about a nerve in a fully engaged position according to an embodiment. Similarly, during the advancement of the electrode cuff 310 from the intermediate open position of FIG. 13 to the fully engaged position during implant of the electrode cuff 310, the distal end 332 of the outer flange member 330 may be positioned along the outer side wall 346 of the second flange member 334 to be spaced further away from the second side wall 328 than when the electrode cuff 310 is in the fully engaged position of FIG. 10, and to be above, rather than below the top wall 332 of the base portion 320. As a result, the diameter of the lumen 340 is increased relative to when the electrode cuff 310 is in the fully engaged position of FIG. 10 prior to being implanted, to accommodate the size of the nerve. Therefore, as illustrated in FIGS. 13 and 14, in order to accommodate the size of the nerve, the first and second flanges 330 and 334 can be advanced or expanded to increase the diameter of the lumen 340.

Figure 15:
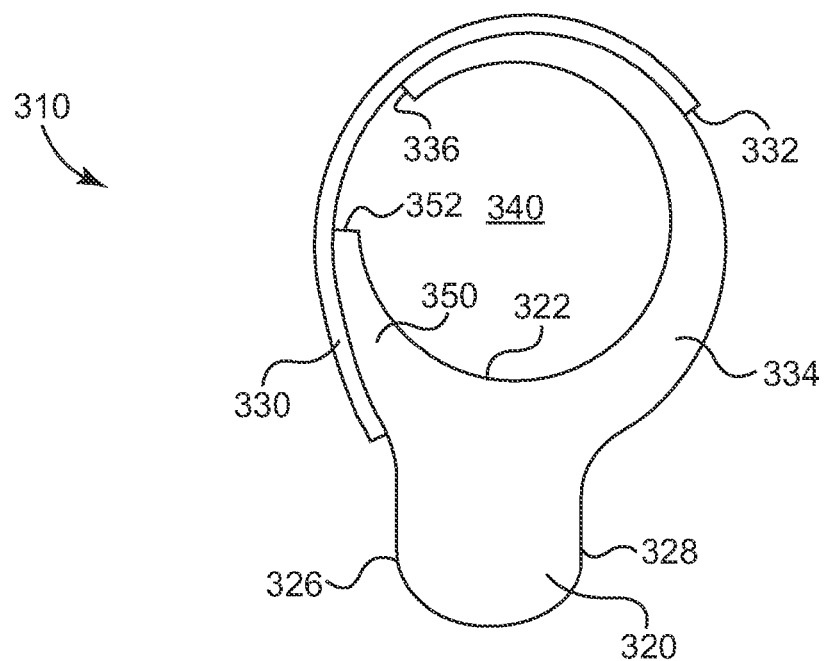
FIG. 15 is a front view of an expandable electrode cuff positioned around a nerve according to an embodiment of the invention.

FIG. 15 is a front view of an expandable electrode cuff positioned around a nerve according to an embodiment of the invention. As illustrated in FIG. 15, according to one embodiment, in order to address the effects of swelling of the hypoglossal nerve 200 that may sometimes occur, particularly after the initial trauma associated with implanting the electrode cuff 310, the first and second flange members 330 and 334 are expandable so that the circumference of the lumen 340 formed by the electrode cuff 310 can be increased to accommodate increases in the diameter of the nerve 200 that occur subsequent to the initial positioning of the expandable electrode cuff 310 about the nerve 200, as illustrated in FIG. 14. For example, during swelling of the nerve 200 subsequent to implant of the device 100, the first flange member 330 and the second flange member 334 expand so that the distal end 332 of the first flange member 330 becomes positioned to be spaced further away from the second side wall 328 of the base portion 320, and to be even further above, rather than below, the top wall 322 of the base portion 320 than when the electrode cuff 310 was initially positioned about the nerve to the position illustrated in FIG. 14. At the same time, the distal end 336 of the second flange member 334 becomes positioned to be spaced further above the distal end 352 of the third flange member 350, and further away from the first side wall 326 and the top wall 322 of the base portion 320, thereby further increasing the size of the lumen 340 to accommodate the swelling. As the swelling of the nerve 200 subsides, the first and second flange members 330 and 334 return towards the original fully engaged position about the nerve 200 that occurred during positioning of the electrode cuff 310 at the time of implant of the device, such as is illustrated in FIG. 14.

By forming the first and second flange members, described above, to extend over the base member so that each of the flange members extend from a proximal end located on one side of the base member to a distal end located along the other side of the base member, the electrode cuff will continue to be positioned completely around the nerve, thereby preventing open gaps from being formed between the distal ends of the flange members as the nerve swells. Rather, the first and second flange members described above enable the necessary expansion of the flange members to accommodate increasing the diameter of the lumen required for maintaining the nerve to be completely enclosed within the lumen. In this way, using the electrode cuff described above, the opportunity for the nerve to extend and extend out of the lumen is decreased, since the electrode cuff is able to more effectively accommodate such swelling.

Figure 16:
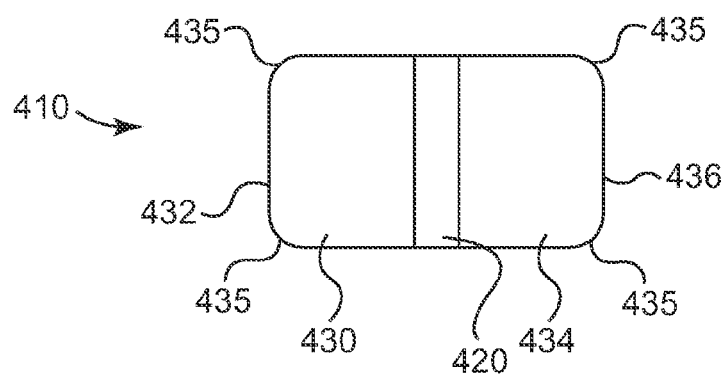
FIG. 16 is a top view of an expandable electrode cuff according to an embodiment of the invention in the fully open position.

FIG. 16 is a top view of an expandable electrode cuff according to an embodiment of the invention in the fully open position. As illustrated in FIG. 16, according to an embodiment, an expandable electrode cuff 410 includes a first flange member 430 and a second flange member 434 extending from a base portion 420, as described above. Ends 432 and 436 of one or both of the first flange member 430 and the second flange member 434, respectively, may include having chamfered corners 435 to prevent the corners 435 from curling during placement of the expandable electrode cuff 410 over the nerve, as described above.

Figure 17:
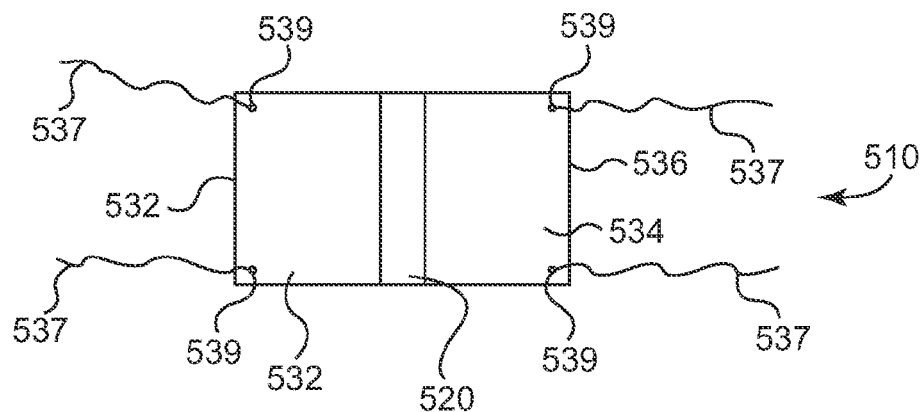
FIG. 17 is a top view of an expandable electrode cuff according to an embodiment of the invention in the fully open position.

FIG. 17 is a top view of an expandable electrode cuff according to an embodiment of the invention in the fully open position. As illustrated in FIG. 17, according to an embodiment, an expandable electrode cuff 510 includes a first flange member 530 and a second flange member 534 extending from a base portion 520, as described above. Ends 532 and 536 of one or both of the first flange member 530 and the second flange member 534, respectively, may include a suture 537 attached thereto. For example, one or more holes 539 may be formed along the ends or at the respective corners 535 for attaching a suture 537 to the flange member. The suture 537 is utilized to pull one or both of the flange members 530 and 534 through and under the nerve during positioning of the electrode cuff 510 about the nerve while in the fully open position. In addition, the sutures 537 may also be utilized to aid in advancing the electrode cuff from the fully engaged position to the fully open position prior to placement of the electrode cuff 510. Once the expandable electrode cuff 510 is positioned under the nerve, the implanter merely releases the hold on the sutures 537 to allow either of the flange members 530 and 534 to be engaged around the nerve, as described above, and the sutures 537 may then be removed by being cut off from the electrode cuff 510.

According to an embodiment, the sutures 537 may come already attached to the electrode cuff, or the electrode cuff may only include the holes formed at one or more of the ends, so that the implanter merely inserts the sutures in the desired holes prior to positioning of the electrode cuff about the nerve.

Figure 18:
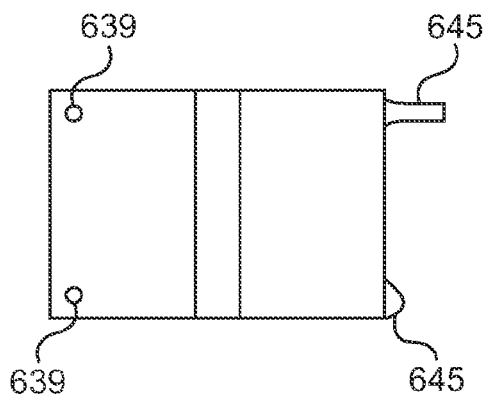
FIG. 18 is a top view of an expandable electrode cuff according to an embodiment of the invention in the fully open position.

FIG. 18 is a top view of an expandable electrode cuff according to an embodiment of the invention in the fully open position. As illustrated in FIG. 18, according to an embodiment, an expandable electrode cuff 610 includes a first flange member 630 and a second flange member 634 extending from a base portion 620, as described above. One or both corners of ends 632 and 636 of one or both of the first flange member 630 and the second flange member 634, respectively, may include a molded or attached tab 645, that, similar to the sutures of FIG. 17, are utilized pull one or both of the flange members 630 and 634 through and under the nerve during positioning of the electrode cuff 610 about the nerve while in the fully open position. In addition, the tabs 645 may also be utilized to aid is advancing the electrode cuff 610 from the fully engaged position to the fully open position prior to placement of the electrode cuff 610. Once the expandable electrode cuff 610 is positioned under the nerve, the implanter merely releases the hold on the tabs 645 to allow either of the flange members 630 and 634 to be engaged around the nerve, as described above.

In addition, an embodiment may include a combination of the tabs 645 and one or more holes 639 formed at the respective corners 635 of the ends 632 and 636 to aid in placement of the electrode cuff about the nerve. If the use of sutures to aid in implant is desired, the implanter may merely inserts a suture in the desired hole 639.

Figure 19:
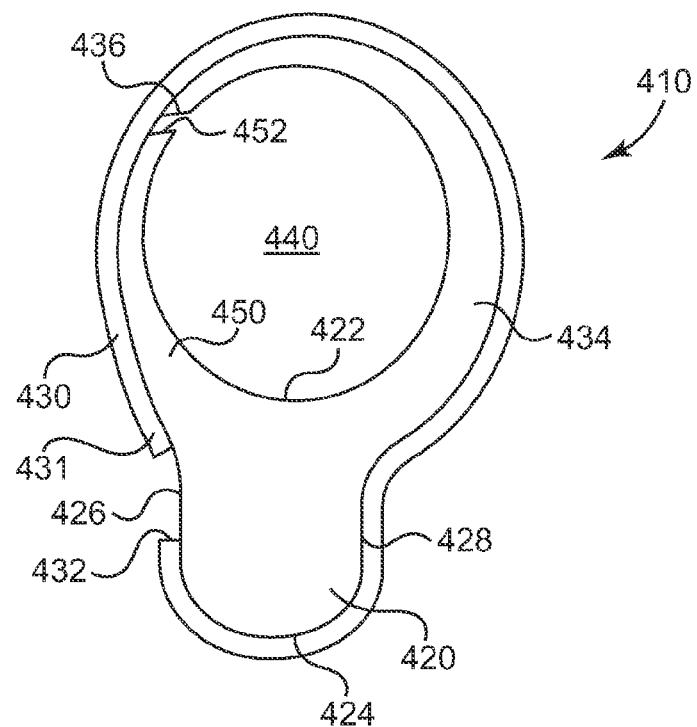
FIGS. 19-21 are front views of an expandable electrode cuff according to embodiments of the invention.
Figure 20:
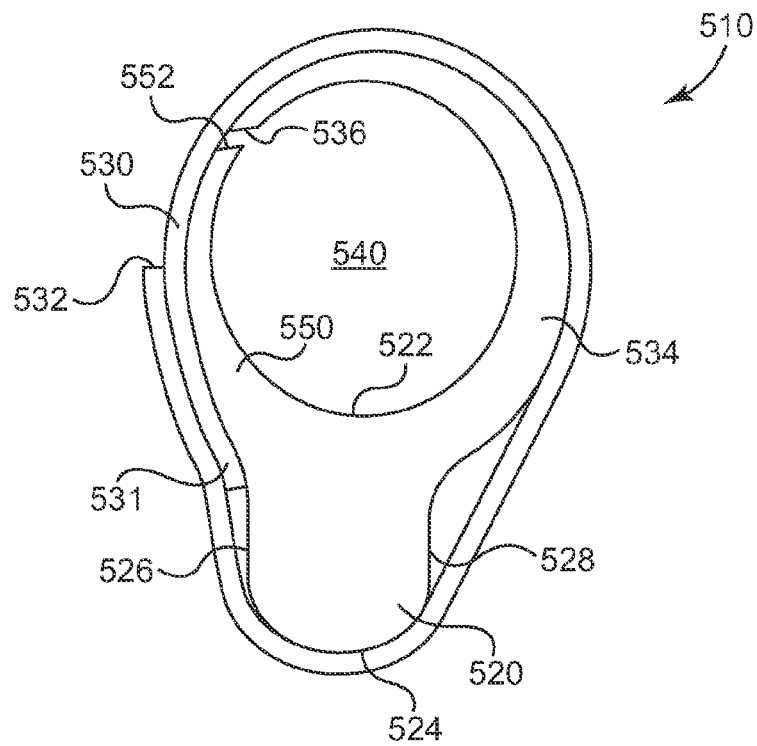
Figure 21:
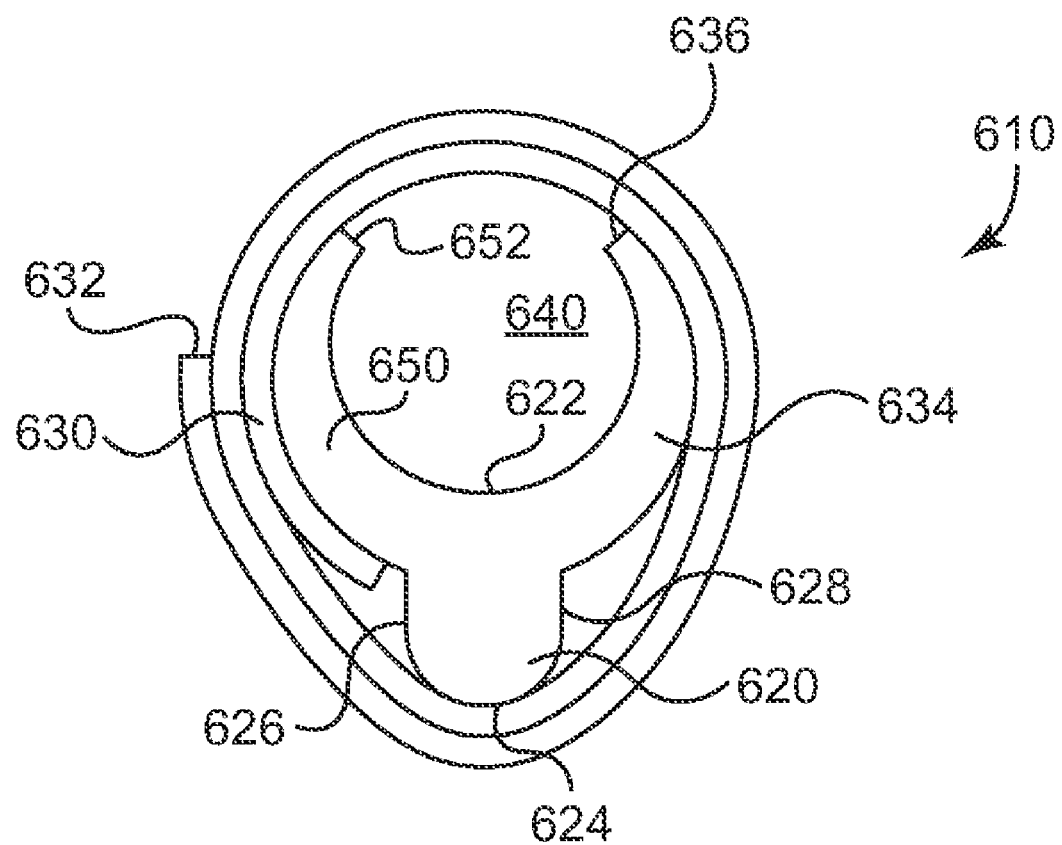

FIGS. 19-21 are front views of an expandable electrode cuff according to embodiments of the invention. As illustrated in FIGS. 19-21, other configurations of the flange members may also be utilized. An electrode cuff 410 according to one embodiment may include a second flange member 434 and a third flange member 450 formed to have any desired lengths to enable the respective ends 436 and 452 to be positioned at any desired location within the lumen 440. For example, as illustrated in FIG. 19, the distal end 436 of the second flange member 434 and the distal end 452 of the third flange member 450 may be positioned further above the first side wall 426 than in the exemplary illustration of FIG. 10. In addition, in another embodiment the length of the first flange member 430 may be increased so that the first flange member 430 extends over the top wall 422 of the base portion 420, around the second flange member 434 and under the bottom wall 424 of the base member 420, with the distal end 432 of the first flange member 430 being positioned below the proximal end 431 of the first flange member 430 along the first side wall 426.

As illustrated in FIG. 20, according to another embodiment, the length of a first flange member 530 may be even further increased so that the first flange member 530 extends over the top wall 522 of the base portion 520, around the second flange member 534, under the bottom wall 524 of the base member 520 and over the first flange member 530 along the proximal end 531 of the first flange member 530, with the distal end 532 of the first flange member 530 being positioned above the proximal end 531 of the first flange member 530 along the first side wall 426.

As illustrated in FIG. 21, according to yet another embodiment, the second flange member 634 and the third flange member 650 may be formed to be symmetrical, with the distal end 636 of the second flange member 634 positioned approximately the same distance above the second side wall 628 of the base portion 620 as the distal end 652 of the third flange member 650 is positioned above the first side wall 626 of the base portion 620. In addition, the length of the first flange member 630 may be increased so that the first flange member 630 extends over the top wall 622 of the base portion 620 a multiple number of times, around the second flange member 434 and under the bottom wall 424 of the base member 420 the multiple number of times, with the distal end 432 of the first flange member 430 being positioned at any location around the electrode cuff 610, such as above the proximal end 431 of the first flange member 430 along the first side wall 426, as shown in FIG. 21.

While at least one exemplary embodiment has been presented in the foregoing detailed description, it should be appreciated that variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

We claim:

1. An expandable electrode cuff of an implantable stimulation system, comprising:

a base member including a first side wall, a second side wall, a top wall and a bottom wall, wherein the first side wall is spaced apart from and generally opposite the second side wall, the top wall is spaced apart from and generally opposite to the bottom wall, and wherein the bottom wall extends from the first side wall to the second side wall; and a first flange member including a proximal end and a first distal end;

a second flange member including a second distal end and a proximal end extending from the second side wall, wherein the second flange member is tapered such that the proximal end of the second flange member has a first thickness substantially greater than a second thickness of the second distal end of the second flange member; and a third flange member including a third distal end and a proximal end extending from the first side wall, wherein the third distal end is positioned above the first side wall of the base member without extending over the top wall of the base member, and wherein the third flange member is tapered such that the proximal end of the third flange member has a first thickness substantially greater than a second thickness of the third distal end of the third flange member, wherein the third flange member, the second flange member, and the base member are formed as a single unitary molded piece, wherein the proximal end of the first flange member is fixedly engaged against the third flange member and the first flange member is biased to extend, from the third flange member, over both the top wall of the base member and the second flange member, and wherein the second flange member is biased to extend over the top wall of the base member to cause the second distal end to be spaced above, and in releasable contact with, the third distal end so that the third flange member and the second flange member form a lumen with the first flange member overlapping both the second and third flange members, and wherein a cross-sectional length of each respective first and second flange member is substantially greater than a cross-sectional length of the third flange member.

2. The expandable electrode cuff of claim 1, wherein the electrode cuff is capable of being advanced between a first position, a second position, and a third position, the first position corresponding to both of the second flange member and the first flange member extending over the top wall of the base member with the first flange member extending in an opposite direction as the second flange member and the first flange member overlapping substantially the entire length of the second flange member, the second position corresponding to the first flange member not extending over the top wall of the base member and the second flange member extending over the top wall of the base member, and the third position corresponding to both of the second flange member and the first flange member not extending over the top wall of the base member.

3. The expandable electrode cuff of claim 1, wherein the first flange member and the second flange member are capable of being advanced between a first position, corresponding to a first diameter of the lumen at initial positioning of the electrode cuff about a nerve, and a second position corresponding to a second diameter greater than the first diameter subsequent to the initial positioning of the electrode cuff about the nerve, wherein in the first position, the first distal end is positioned a first distance above the second side wall of the base member and the second distal end is positioned a second distance above the third distal end, and wherein in the second position, the first distal end is positioned a third distance greater than the first distance above the second side wall of the base member and the second distal end is positioned a fourth distance greater than the second distance above the third distal end.

4. The expandable electrode cuff of claim 1, wherein the first thickness is at least one order of magnitude greater than the second thickness.

5. The expandable electrode cuff of claim 1, further comprising means for pulling one or both of the first flange member and the second flange member under a nerve during positioning of the expandable electrode cuff about the nerve.

6. The expandable electrode cuff of claim 1, and further comprising an implantable stimulation system comprising:
an implantable pulse generator;
a stimulation lead having a lead body extending from a lead body proximal end to a lead body distal end; and
a connector positioned at the lead body proximal end for electrically connecting the stimulation lead and the implantable pulse generator,
wherein the expandable electrode cuff is positioned at, and supported by, the lead body distal end.

7. The expandable electrode cuff of claim 1, wherein the point of releasable contact between the third distal end and the second distal end is located laterally of the first side wall of the base member.

8. The expandable electrode cuff of claim 1, wherein at least the third and second flange members are formed of a memory-based material and in a shape that biases the third and second flange members to form, prior to engagement about a nerve, a lumen in which the second distal end is in releasable contact with the third distal end.

9. The expandable electrode cuff of claim 1, wherein the length of the first flange member is configured to position the first flange member to overlap substantially the entire length of the second flange member.

10. The expandable electrode cuff of claim 1, wherein a portion of the base member, including a portion of the respective first and second side walls, extends generally outward and away from a proximal end of the third flange member and from a proximal end of the second flange, respectively.

* * * * *